United States Patent
Huffman

(10) Patent No.: US 8,662,782 B2
(45) Date of Patent: Mar. 4, 2014

(54) SURFACE CLEANING DEVICE WITH A BLEACH GENERATOR

(75) Inventor: Eric C. Huffman, Lowell, MI (US)

(73) Assignee: BISSELL Homecare, Inc., Grand Rapids, MI (US)

( * ) Notice: Subject to any disclaimer, the term of this patent is extended or adjusted under 35 U.S.C. 154(b) by 1196 days.

(21) Appl. No.: 12/239,198

(22) Filed: Sep. 26, 2008

(65) Prior Publication Data

US 2010/0078318 A1   Apr. 1, 2010

(51) Int. Cl.
| | |
|---|---|
| A46B 11/00 | (2006.01) |
| A47K 7/02 | (2006.01) |
| B43K 8/10 | (2006.01) |
| A47L 13/22 | (2006.01) |

(52) U.S. Cl.
USPC ............ 401/283; 401/140; 401/266; 401/130

(58) Field of Classification Search
USPC .......................... 401/140, 201, 283, 266, 130
See application file for complete search history.

(56) References Cited

U.S. PATENT DOCUMENTS

| | | | | |
|---|---|---|---|---|
| 2,701,790 | A | | 2/1955 | Goument |
| 3,819,329 | A | * | 6/1974 | Kaestner et al. .................. 422/3 |
| 4,609,450 | A | * | 9/1986 | Seimiya et al. .............. 204/217 |
| 4,810,343 | A | * | 3/1989 | Bonnardel ................ 204/224 R |
| 5,833,675 | A | * | 11/1998 | Garcia ............................ 604/310 |
| 5,964,990 | A | * | 10/1999 | Muratori et al. ......... 204/224 M |
| 6,368,472 | B1 | | 4/2002 | McGuire |
| 6,524,475 | B1 | | 2/2003 | Herrington et al. |
| 6,638,364 | B2 | | 10/2003 | Harkins et al. |
| 6,719,891 | B2 | * | 4/2004 | Ruhr et al. ..................... 205/500 |
| 6,843,895 | B2 | | 1/2005 | Bakir et al. |
| 7,008,523 | B2 | | 3/2006 | Herrington |
| 7,156,962 | B2 | | 1/2007 | Koizumi et al. |
| 2002/0168216 | A1 | * | 11/2002 | Policicchio et al. .......... 401/270 |
| 2004/0267190 | A1 | | 12/2004 | Tamarkin et al. |
| 2005/0194261 | A1 | | 9/2005 | Hadia |
| 2005/0230267 | A1 | * | 10/2005 | Veatch et al. ................. 205/687 |
| 2006/0086622 | A1 | | 4/2006 | Prior |
| 2006/0101604 | A1 | | 5/2006 | Frederick et al. |
| 2007/0186368 | A1 | * | 8/2007 | Field et al. ....................... 15/320 |

FOREIGN PATENT DOCUMENTS

| | | |
|---|---|---|
| CA | 1120664 A2 | 3/1982 |
| GB | 2379866 A | 3/2003 |
| WO | 2004084698 A2 | 10/2004 |
| WO | 2005092017 A2 | 10/2005 |
| WO | 2009011841 A1 | 1/2009 |

* cited by examiner

*Primary Examiner* — Justin Jonaitis
(74) *Attorney, Agent, or Firm* — McGarry Bair PC

(57) ABSTRACT

According to the invention, a surface cleaning device comprises an electrolytic cell for generating bleach for use with a cleaning pad. The electrolytic cell is in fluid communication with the cleaning pad for delivering bleach to a surface to be cleaned. According to another embodiment of the invention, the surface cleaning device is a hand-held cleaning device capable of selectively generating bleach at the request of a user directly in the cleaning pad. A sufficient amount of bleach for cleaning a surface can be generated within the electrolytic cell at the request of a user, eliminating the need for storing and transporting large quantities of bleach.

26 Claims, 4 Drawing Sheets

SURFACE CLEANING DEVICE WITH A BLEACH GENERATOR

BACKGROUND OF THE INVENTION

1. Field of the Invention

The invention relates to a method and apparatus for selectively generating bleach for use with a surface cleaning device.

2. Description of Related Art

Oxidizing agents, such as chlorine bleach, for example, are well known for their uses in cleaning and disinfecting materials and surfaces. However, this property also makes the handling, storage and transportation of these chemicals hazardous, especially in a consumer setting such as a residential household. Therefore, it is advantageous to have a system that is able to generate small amounts of an oxidizing agent, such as bleach, at the point of use or on demand, from chemicals that pose no health or safety concerns.

Bleach, whose active ingredient is sodium hypochlorite, can be generated in an electrolytic cell from water and sodium chloride, non-hazardous chemicals. An example of an electrolytic cell for generating sodium hypochlorite is disclosed in U.S. Pat. No. 2,707,790 to Goument. In an electrolytic cell, an external power source is required to initiate the oxidation and reduction reactions that take place at the electrodes. In an electrolytic cell for generating sodium hypochlorite, an electrical potential is applied across the electrodes. An oxidation reaction takes place at the anode, producing chlorine gas and a reduction reaction takes place at the cathode, producing sodium hydroxide. The chlorine gas and sodium hydroxide react to produce sodium hypochlorite. Electrolytic cells of this nature can be made in a variety of sizes from those suitable for use in an industrial scale to a size suitable for use in a residential setting.

Several systems have been disclosed for generating an oxidizing agent at the point of use in an electrolytic cell and spraying the generated agent onto a surface to be cleaned and disinfected. For example, U.S. Pat. No. 3,819,329 to Kaestner et al. discloses a spray sanitizing system that includes an electrolytic cell for instantaneously generating a bactericidal solution wherein the chlorine is substantially in the form of hypochlorous acid rather than hypochlorite by maintaining a low pH. This solution can then be sprayed onto a surface to be cleaned with a hand operable wand. U.S. Pat. No. 6,638,364 to Harkins et al. discloses a vacuum cleaning system for generating electrolyzed alkaline water from an electrolytic cell comprising sodium chloride and water. The electrolyzed alkaline water is sprayed onto a surface to be cleaned and then removed from the surface by suction means. These systems are fairly large and require a wheeled platform or vehicle for transporting the system to different areas to be cleaned.

U.S. Pat. No. 7,008,523 to Herrington and U.S. Pat. No. 7,156,962 Koizumi et al. to disclose an electrolytic system for generating an oxidizing agent at the point of use in a dispenser such as a spray bottle. The Herrington '523 patent discloses an electrolytic cell comprising water and sodium chloride for generating bleach. The bleach can be generated in a separate reservoir and delivered to the dispenser or the bleach can be generated directly in the dispenser. The Koizumi et al. '962 patent discloses an electrolytic cell for generating ozone or active oxygen at the point of use for disinfecting surfaces. The electrolytic cell can be placed in a dispenser such as a spray bottle for generating the ozone or active oxygen directly in the dispenser.

The prior systems discussed above deliver the oxidizing agent generated in the electrolytic cell to a surface to be cleaned by spraying the solution onto the surface. One common form of cleaning in a residential household uses a cleaning pad, such as is used for cleaning bare floors or for scrubbing hard surfaces such as a bathtub or sink. Thus, cleaning pads can be used with these prior systems. However, spraying bleach onto a surface may be hazardous if not carefully applied.

SUMMARY OF THE INVENTION

According to one embodiment of the invention, a surface cleaning device comprises a source for an electrolyte solution and a cleaning pad in fluid communication with the source for delivering a cleaning fluid to a surface to be cleaned. The surface cleaning device further comprises an electrolytic cell comprising at least one anode and at least one cathode, with the at least one anode and the at least one cathode formed at least in part in the cleaning pad, for generating a bleach solution within the cleaning pad for application by the cleaning pad to the surface to be cleaned and a cleaning head, wherein the cleaning pad is mounted to the cleaning head and the at least one anode and at least one cathode are mounted to the cleaning head and extend at least partially into the cleaning pad for generating the bleach solution in situ in the cleaning pad.

In yet another embodiment, the source comprises a refillable tank and there may be a salt chamber for holding salt for making an electrolyte solution when water passes through the salt chamber. The salt chamber has an inlet opening connected to the refillable tank and an outlet opening connected to the electrolytic cell.

According to another embodiment, the source can include the cleaning pad or the source can be a tank that is separated from the cleaning pad.

In one embodiment, a sensor for determining a characteristic of the electrolytic cell related to the amount of bleach is associated with the electrolytic cell. The characteristic of the electrolytic cell can be one of a temperature, pH or potential of the electrolyte solution. Preferably, the sensor is connected to an indicator for informing the user of the amount of bleach in the electrolytic cell. Preferably, the indicator is adapted to inform the user when the concentration of bleach in the electrolytic cell reaches a predetermined value. Alternatively, the indicator is adapted to inform the user of a range of concentration of bleach in the electrolytic cell.

In a further embodiment, a controller is connected to the sensor and the indicator and the controller has a program for comparing a signal from the sensor with stored acceptable values or ranges of values and generating a display signal representative of the concentration of bleach in the electrolytic cell.

In another embodiment, a foot assembly mounts the cleaning pad and a handle assembly is pivotally mounted to the foot assembly, and the source forms a part of the handle assembly.

In yet another embodiment, a housing adapted to be held in the user's hand includes a power supply housing and a cleaning head with the cleaning pad is mounted to the cleaning head. In this embodiment, the at least one anode and at least one cathode are connected to a power supply and are positioned at least partially within the cleaning pad, whereby the electrolytic cell is formed at least in part in the cleaning pad. The cleaning pad can be a sponge that is adapted to hold the electrolyte solution. The housing can include a tank for a cleaning solution and the tank can be fluidly connected to the cleaning pad. The power supply can be a rechargeable battery, a disposable battery or derived from a power outlet.

In another embodiment, the surface cleaning device further comprises an actuator connected to the electrolytic cell for selectively controlling the generation of bleach. The surface cleaning device can further include an electric pump, a squeeze pump or a gravity pump to move the electrolyte solution between the source and the cleaning pad.

In yet another embodiment, the electrolyte solution is a mixture of sodium chloride and water. The electrolyte solution can further include a detergent.

The invention provides a sufficient amount of bleach for cleaning a surface that can be generated within the electrolytic cell at the request of a user, eliminating the need for storing and transporting large quantities of bleach.

DESCRIPTION OF THE PREFERRED EMBODIMENT

Figure 1:
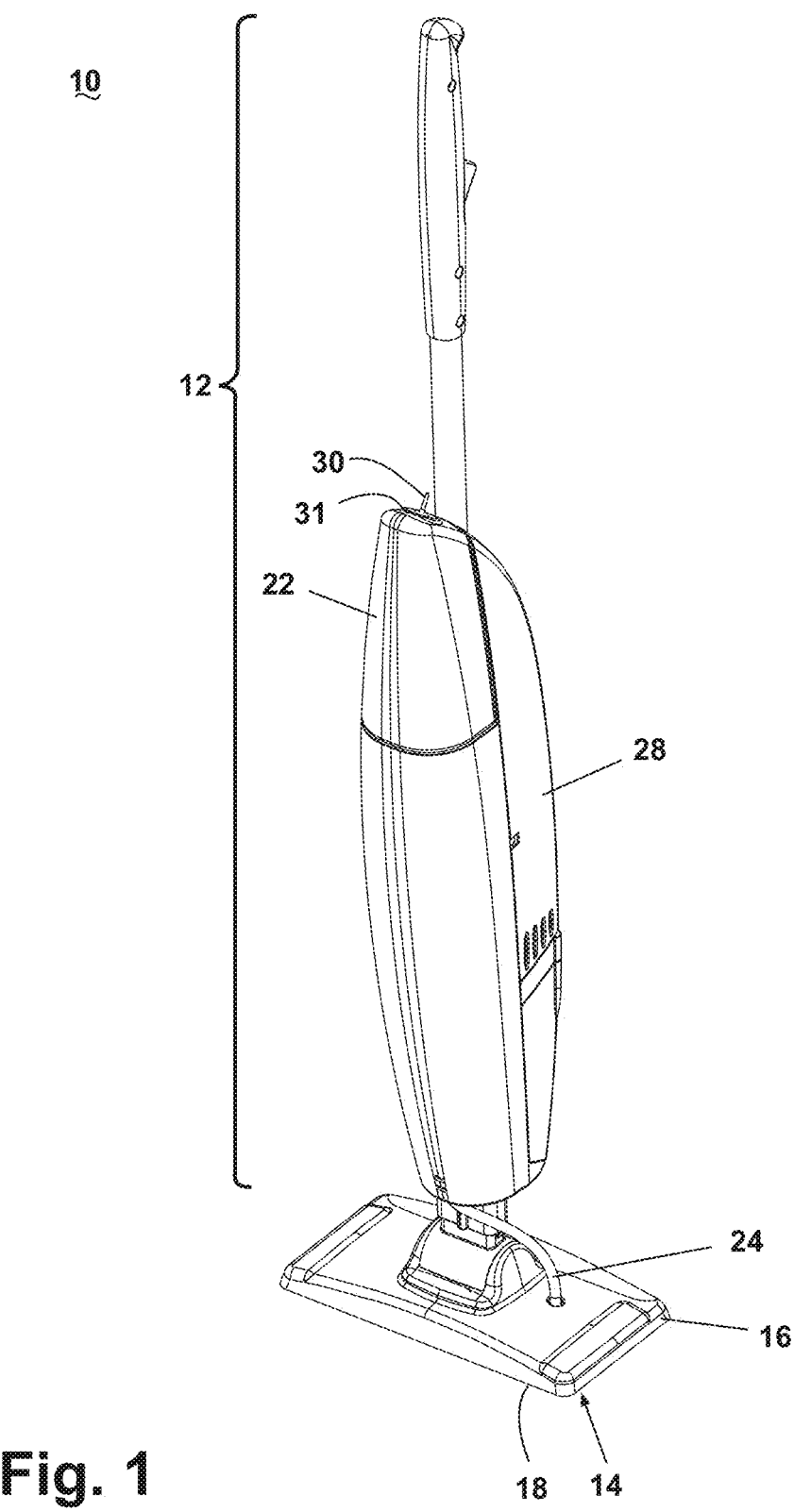
FIG. 1 is a perspective view of a stick-mounted cleaning device capable of selectively generating bleach according to an embodiment of the invention.

FIG. 1 illustrates a stick-mounted cleaning device such as a bare floor cleaning device 10 according to an embodiment of the invention. The cleaning device 10 comprises a handle assembly 12 pivotally mounted to a foot assembly 14. The foot assembly comprises a cleaning head 16 for mounting a cleaning pad 18, such as a sponge or absorbent pad, for example. A bleach generating and dispensing system 20 is located within a housing 22. The cleaning pad 18 is fluidly connected with the bleach generating and dispensing system 20 by a fluid conduit 24 for receiving bleach and/or a cleaning solution from the dispensing system 20. A power supply 26 in the form of standard dry cell or rechargeable batteries can be mounted within a housing 28. One or more actuator switches 30 on a display panel 31 can be connected with a controller 32 for selectively controlling the bleach generating and dispensing system 20.

Figure 2:
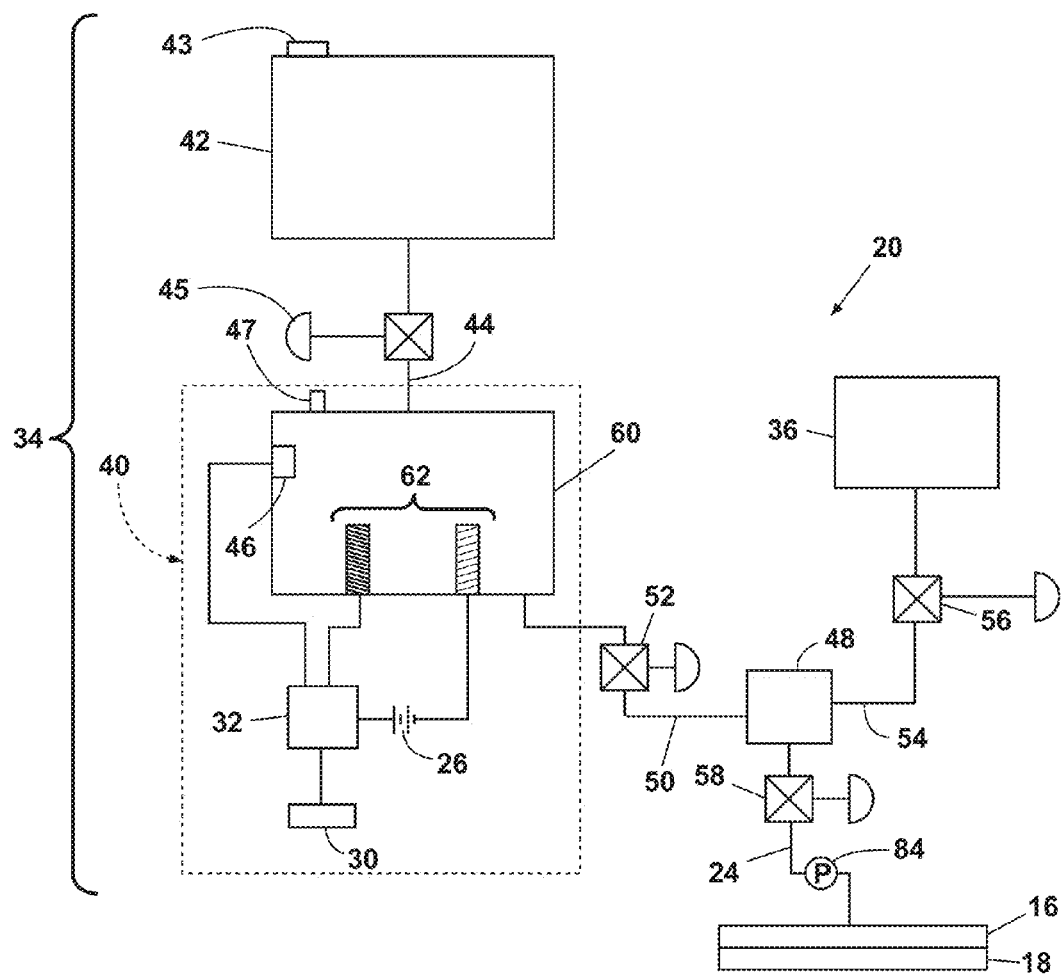
FIG. 2 is a schematic diagram of a bleach generating and cleaning solution dispensing system for use with the stick-mounted cleaning device of FIG. 1 according to an embodiment of the invention.

FIG. 2 is a block schematic representation of the bleach generating and dispensing system 20. The bleach generating and dispensing system 20 comprises an on-demand bleach generating system 34 having an electrolytic cell 40 fluidly coupled with an electrolyte reservoir 42. The bleach generating and dispensing system 20 can also be connected with a cleaning composition reservoir 36. The cleaning composition reservoir 36 can be used for storing a cleaning composition to be dispensed through the dispensing system 20 or through a separate fluid dispensing system.

The invention is not limited to a cleaning device 10 comprising a separate cleaning composition reservoir. In alternative embodiment, the cleaning composition can be added to the electrolyte reservoir 42 and dispensed with the bleach solution generated in the bleach generating system 34.

The cleaning solution, regardless of whether it is stored in a separate cleaning composition reservoir 36 or it is added to the electrolyte reservoir 42, can comprise any cleaning solution containing, but not limited to components such as water, a detergent, a surfactant, a solvent and a fragrance. Alternatively, the cleaning solution can just be water.

The bleach generating and dispensing system 20 further comprises an electrolytic cell 40 for selectively generating bleach at the request of a user. The electrolytic cell 40 is fluidly connected with an electrolyte storage reservoir 42 by a fluid supply conduit 44. The electrolyte storage reservoir 42 is provided with a resealable opening 43 for receiving materials such as an electrolyte or a cleaning solution. The resealable opening can be in the form of a threaded aperture that receives a screw cap, for example. A valve 45 can be coupled with the fluid conduit 44 for controlling the flow of liquid through the conduit 44.

The electrolytic cell 40 comprises a reaction reservoir 60 for receiving an electrolyte composition and at least two electrodes 62. The reaction reservoir 60 can comprise a container having walls that physically separate the electrodes and reactants from the surroundings, as illustrated in FIG. 2. Alternatively, the reaction reservoir 60 can comprise the area in which the reactants are confined during the bleach generating process, such as will be described below. The electrolyte composition can be in the form of a solid, liquid, gel or slurry that the user places in the electrolyte storage reservoir 42 or directly in the reaction reservoir 60. The electrolytic cell 40 can further comprise a pressure vent 47 for releasing any pressure increase that can occur during the course of the bleach generating process.

At least one of the electrodes 62 is a cathode 64 and at least one of the electrodes 62 is an anode 66. The electrodes 62 can be completely or partially located within the reaction reservoir 60. The electrodes 62 can be connected with the power supply 26 through the controller 32. The power supply 26 can deliver a controlled electrical potential to the electrodes 62 for producing an oxidation-reduction reaction in the electrolytic cell 40. The oxidation-reduction reaction can directly or indirectly generate an oxidant, such as bleach.

The electrolytic cell 40 is connected with the controller 32 and the power supply 26 for delivering a controlled electrical potential to the electrolytic cell 40. The delivery of an electrical potential to the electrolytic cell 40 is initiated by the user through the activation of an actuator switch 30 on the display panel 31 which activates the controller 32.

The controller 32 can be communicably coupled with the electrolytic cell 40 and other components of the cleaning device 10 for generating a bleach solution and delivering the bleach solution and/or cleaning solution to the cleaning pad 18 for cleaning and disinfecting a surface. The controller 32 can be connected with the electrolytic cell 40 to control the application of a potential to the electrolytic cell 40 and for receiving sensor data from one or more sensors 46. The controller 32 can have a micro-processor for executing software to analyze the sensor data to determine one or more properties of the electrolytic cell 40. The controller 32 can also have an internal and/or external memory in which the analysis software can be stored. The controller 32 can also be connected with other components of the bleach generating and dispensing system 20 such as the electrolyte reservoir 42, the cleaning composition reservoir 36 and one or more valves for controlling the flow of liquid within the cleaning device 10.

The sensor 46 can be connected with the electrolytic cell 40 and the controller 32 for measuring one or more characteristics of the electrolytic cell 40, such as the temperature, pressure, pH and potential of the electrolyte composition. The one or more characteristics of the electrolytic cell 40 can be used by the controller 32 to determine one or more properties of the electrolytic cell 40 such as the status of the bleach generating reaction, the amount of reactants or bleach present, the status of the electrodes 62, low or high electrolyte concentration, or low fluid levels for example. The sensor 46 can comprise one or more sensors such as a pH sensor, an oxidation-reduction potential (ORP) sensor, a pressure sensor, or a temperature sensor, for example.

The electrolytic cell 40 can be directly connected with the fluid conduit 24 for delivering the bleach solution to the cleaning pad 18 or it can be connected with the fluid conduit 24 through a mixing reservoir 48. The mixing reservoir 48 can be connected with the bleach generating system 34 by a fluid conduit 50 controlled by a valve 52. The mixing reservoir 48 can also be connected with the cleaning composition reservoir 36 by a fluid conduit 54 controlled by a valve 56. A valve 58 can be provided for controlling the flow of fluid from the mixing reservoir 48 to the cleaning pad 18 through the fluid conduit 24. The valve 58 can be controlled manually by the user through a knob or trigger, for example, or the valve 58 can be controlled by the controller 32.

All or some of the valves within the bleach generating and dispensing system 20 can be controlled manually by the user or automatically via the controller 32. Switches, knobs, triggers, or, any other suitable control means can be located on the handle assembly 12 to provide the user with means to manually operate the fluid flow control valves. The valves can be any suitable type of fluid flow control valve such as a check valve or a solenoid valve, for example.

Figure 3:
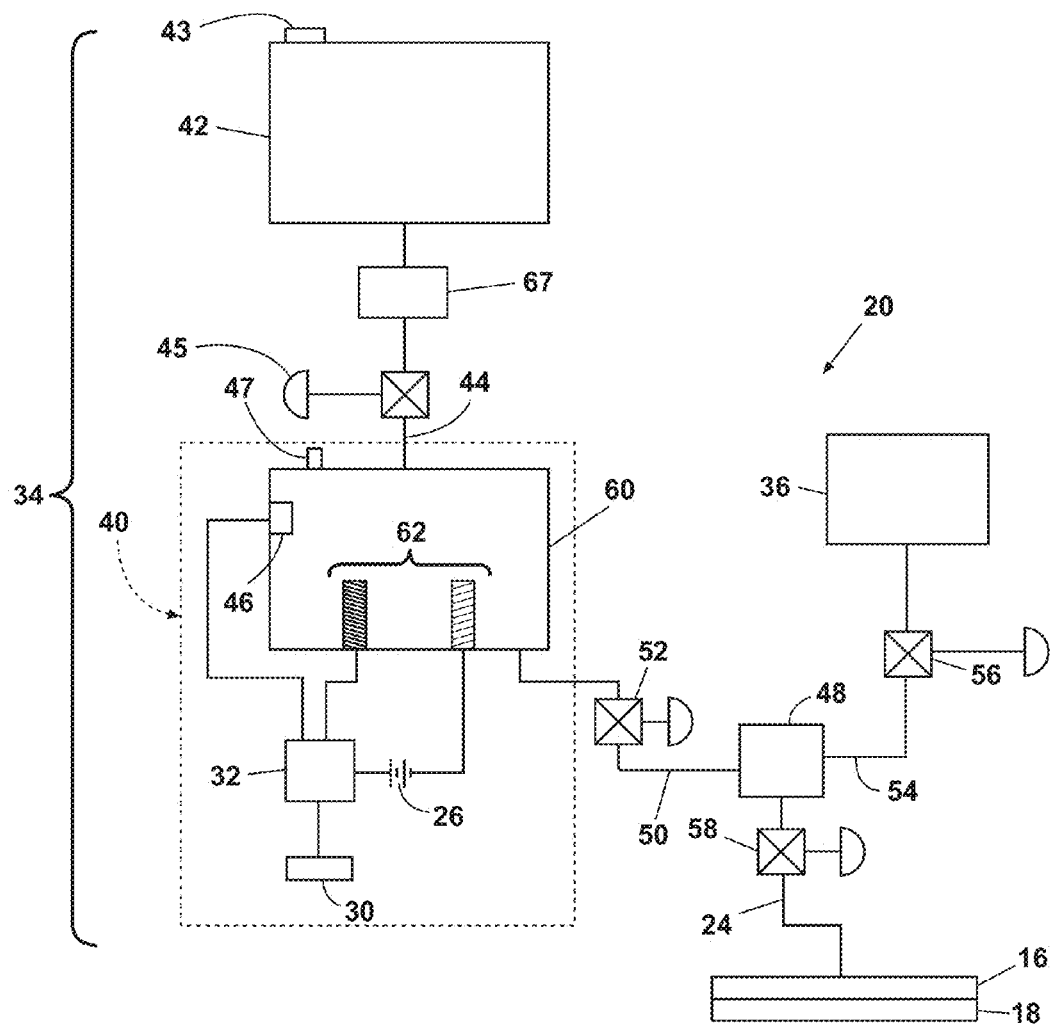
FIG. 3 is a schematic diagram of a bleach generating and cleaning solution dispensing system for use with the stick-mounted cleaning device of FIG. 1 according to another embodiment of the invention.

The electrolyte solution, bleach solution and/or the cleaning solution can be moved through the dispensing system 20 by any suitable means such as with one or more pumps 84, such as an electric pump or squeeze pumps, as illustrated in FIG. 2, or a gravity flow systems, such as is illustrated in FIG. 3, or any combination thereof.

Referring now to FIG. 3, where like numerals are used to designate like parts, the bleach generating and dispensing system 20 can also comprise a removable and/or refillable salt chamber 67. The salt chamber 67 can be fluidly coupled with the reservoir 42 and the reaction reservoir 60 through the fluid conduit 44. The valve 45 can be positioned along the fluid conduit 44 to control the flow of liquid from the reservoir 42 to the salt chamber 67 or to control the flow of liquid from the salt chamber 67 to the reaction reservoir 60, as illustrated in FIG. 3. Alternatively, two valves 45 can be positioned along the fluid conduit 44, one upstream of the salt chamber 67 and one downstream of the salt chamber 67, to control both the flow of liquid from the reservoir 42 and from the salt chamber 67.

The salt chamber 67 can comprise a salt composition in the form of a solid, concentrated slurry or a gel. For example, the salt composition in the salt chamber 67 can be in the form of a solid block of salt or solid pellets of various sizes.

When the user desires to generate bleach, the user can activate a switch on the display panel 31 to activate the controller 32 to deliver a controlled electrical potential from the power supply 26 to the electrodes 62. The electrical potential initiates an oxidation-reduction reaction between the electrolyte composition and the electrodes 62. When the electrolyte composition is in the form of a mixture of sodium chloride and water, a reduction reaction takes place near the cathode 62 to produce ammonium hydroxide; an oxidation reaction takes place near the anode 64 to produce chlorine gas. The chlorine gas and ammonium hydroxide react to produce sodium hypochlorite, an oxidant, the active component of bleach.

The generated bleach can be delivered to the cleaning pad 18 directly through fluid conduit 24 or it can first be combined with a cleaning composition stored in the cleaning composition reservoir 36 in the mixing reservoir 48 and then delivered to the cleaning pad 18. The bleach generating process is ended when the delivery of the electrical potential from the power supply 26 to the electrodes 62 is terminated.

The electrolytic cell 40 can be set-up to produce other oxidants depending on the contents of the cell and the electrodes. The production of other oxidants can require the cathode 64, the anode 66 and the reactants to be housed within separate reservoirs or separated by an impermeable or semi-permeable membrane. Such electrolytic cells are known in the art and can include additional components, such as a salt bridge or a catalyst, for example.

There are several ways by which the user can supply the bleach generating system 34 with the electrolytes for generating the bleach solution. For example, the user can add a pre-made solution of cleaning solution and electrolytes to the electrolyte reservoir 42 through the re-sealable opening 43. Alternatively, the user can prepare the electrolyte solution in the reservoir 42 by adding the cleaning solution and the electrolytes separately. The electrolytes can be in the form of a solid, a liquid concentrate, a slurry or a gel. The electrolytes can be individually packaged in pre-measured amounts or packaged in bulk and measured by the user.

According to the embodiment illustrated in FIG. 3, the cleaning solution can be added to the reservoir 42 and then allowed to flow through the salt chamber 67 to the reaction reservoir 60. As the solution flows through the salt chamber 67, some of the electrolytes dissolve into the solution, providing the solution with the electrolytes for generating bleach in the electrolytic cell 40. This embodiment provides for storage of the salt on-board the cleaning device 10.

Figure 4:
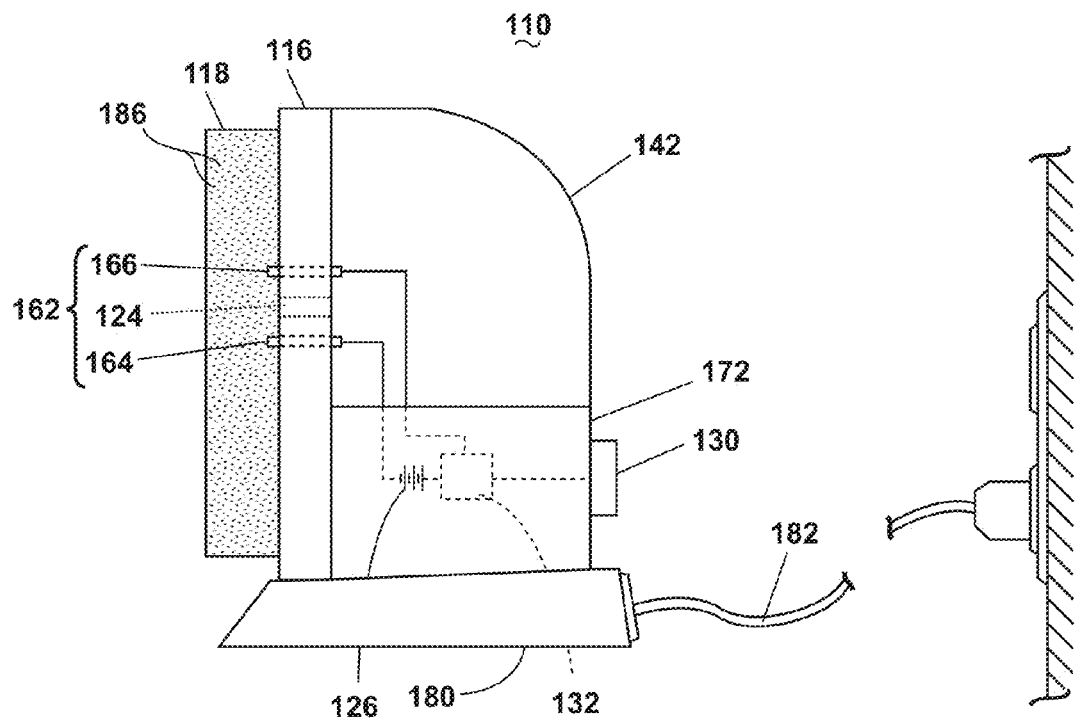
FIG. 4 is a side view of a hand-held cleaning device capable of selectively generating bleach according to an embodiment of the invention.
Figure 5:
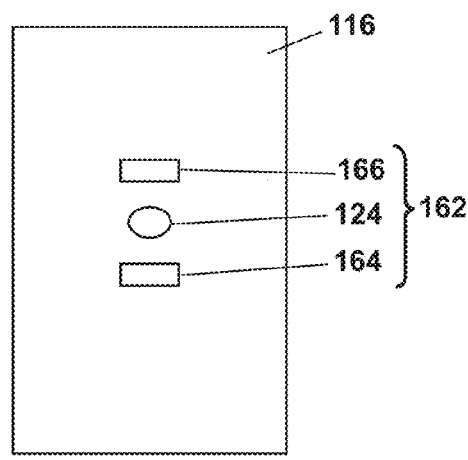
FIG. 5 is a plan view of a cleaning head of the hand-held cleaning device of FIG. 4 and with a cleaning pad removed.

FIG. 4 illustrates another embodiment of the invention wherein a bleach generating and dispensing system 120 is incorporated into a hand-held cleaning device 110. The bleach generating and dispensing system 120 is similar to the bleach generating and dispensing system 12 except that it is incorporated into a hand-held cleaning device 110 instead of a stick-mounted cleaning device 10. Therefore, elements in the bleach generating and dispensing system 120 similar to those of the bleach generating and dispensing system 20 will be numbered with the prefix 100. While the elements of the bleach generating and dispensing system 120 are illustrated with the hand-held cleaning device 110, they may also be used with the stick-mounted cleaning device 10.

The hand-held cleaning device 110 comprises a reservoir 142, a power supply housing 172 and a cleaning head 116. A cleaning pad 118 is mounted to the hand-held cleaning device 110 by the cleaning head 116. The cleaning pad 118 comprises one or more layers of an absorbent material with sodium chloride 186 absorbed or embedded within the one or more layers of the cleaning pad 118. The user can introduce a cleaning solution to the reservoir 142 through a re-sealable opening prior to starting the cleaning process (not shown). The cleaning solution can comprise any cleaning solution containing, but not limited to components such as water, a detergent, a surfactant, a solvent and a fragrance. Alternatively, the cleaning solution can just be water.

The contents of the reservoir 142 are fluidly connected with the cleaning pad 118 through a conduit, nozzle or aperture 124 connected with the reservoir 142 and the cleaning head 116. The cleaning head 116 can comprise one conduit 124, as illustrated, or any suitable number of conduits 24.

It is also within the scope of the invention for the hand-held cleaning device 110 to not have a reservoir 142. When the hand-held cleaning device 110 does not have a reservoir 110, cleaning solution can be added directly to the cleaning pad 118.

The hand-held cleaning device 110 is provided with an electrolytic cell 140 for generating an oxidant, such as bleach for example, as described above in reference to the electrolytic cell 40. Similar to the electrolytic cell 40, the electrolytic cell 140 comprises two or more electrodes 162 extending through the cleaning head 116. The electrodes 162 can be located adjacent a surface of the cleaning pad 118 or the electrodes 162 can extend partially or fully into the cleaning pad 118. At least one of the electrodes 162 is a cathode 164 and at least one of the electrodes 162 is an anode 166. The electrodes 162 are connected with a power supply 126 and a controller 132 located within the power supply housing 172.

The controller 132 can be communicably coupled with the electrolytic cell 140 and an actuator button 130 for selectively generating bleach within the electrolytic cell 140. The controller 132 can be connected with the actuator button 130 such that actuation of the actuator button 130 activates the controller 132 to deliver a controlled potential to the electrolytic cell 140 to initiate an oxidation-reduction reaction that generates bleach.

The power supply 26 can be in the form of conventional dry cell batteries that can be disposable or rechargeable. The cleaning device 110 can also be provided with a charging base unit 180 that plugs directly into a common household electrical outlet through a cord 182 for charging rechargeable batteries through a well-known charging circuit.

The user can start the cleaning process by removing the hand-held cleaning unit 110 from the base unit 180 and filling the reservoir 142 with cleaning solution. The user can then activate the electrolytic cell 140 by pressing the actuator button 130. While the electrolytes are contained within the cleaning pad 118, bleach will not be generated until water is supplied to the cleaning pad 118 to react with the electrolytes. The water can be supplied to the electrolytic cell 140 in the form of the cleaning solution that is stored in the reservoir 142. The cleaning solution can be released from the reservoir 142 by the user by squeezing the reservoir 142 or applying downward pressure to the cleaning device 110. The cleaning device 110 can also be provided with a valve mechanism that the user can selectively engage to release the cleaning solution from the reservoir 142 to the cleaning pad 118.

Once the cleaning solution is delivered to the cleaning pad 118, the oxidation-reduction reaction of water and sodium chloride can take place and bleach is generated in the cleaning pad 118. The bleach can be delivered to the surface being cleaned by the user as the cleaning device 110 is moved over the surface in the course of the cleaning process. When the user has completed the cleaning process, the actuator button 130 can be pressed again and the delivery of an electrical potential to the electrodes 162 is terminated. Without the application of an electrical potential to the electrodes 162, the electrolytic cell 140 will stop generating bleach.

According to another embodiment, the electrodes 162 of the embodiment of the invention illustrated in FIG. 4 can also be located entirely within the reservoir 142. The electrolyte and cleaning solution can both be added to the reservoir 142 and the bleach generating process can take place entirely within the reservoir 142. The generated bleach can then be delivered to the cleaning pad 118 rather than being generated within the cleaning pad 118. In this embodiment, the electrodes 162 can protrude from the cleaning head 116 and can be in contact with a face of the cleaning pad 118 or can extend partially or fully into the cleaning pad 118.

The electrolytes can be in the form of a solid, liquid, gel or a slurry of sodium chloride or other electrolytic substance. The electrolytes and the cleaning solution can be supplied to the user in a pre-mixed form or the user can add the electrolytes and the cleaning solution to the reservoir 142 separately.

According to another embodiment of the invention, the hand-held cleaning device 110 can be used without a reservoir 142. The sodium chloride can be stored within the cleaning pad 118 and the cleaning solution can be added prior to or during the cleaning process. The cleaning pad 118 can be made from one or more layers of absorbent materials with the sodium chloride stored within the one or more layers. The electrodes 162 can extend beyond the cleaning head 116 and can be in contact with a face of the cleaning pad 118 or extend partially or fully into the cleaning pad 118. The cleaning solution can be added to the cleaning pad 118 by the user prior to generating the bleach solution or during the cleaning process. For example, the user can pre-wet the cleaning pad 118 in a body of standing cleaning solution, such as in a bucket, or under a flow of water, such as produced by a faucet. Once the user has wet the cleaning pad 118, he or she can selectively generate the bleach solution by pressing the actuator 130. The user can then commence the cleaning process.

The cleaning pad 118 can also be wet during the cleaning process. For example, the user can start the bleach generating process by pressing the actuator 130 as the user moves the cleaning pad 118 over a wet surface. The bleach will be generated as the cleaning pad 118 absorbs water as it is moved over the wet surface. Additionally, the cleaning solution can be stored in separate reservoir connected with the cleaning pad 18 and released by the user prior to or during the cleaning process.

The cleaning pads 18, 118 can be selectively removed by the user for washing, replacement or interchanged with a cleaning pad providing different features, such as an abrasive surface or a tapered shape, for example, suitable for a variety of cleaning environments and scenarios. The cleaning pads 18, 118 can be removably connected with the cleaning heads 16, 116, respectively, by any suitable mechanical connectors such as screws, hooks, straps, clamps or hook and loop tape, such as Velcro® hook and loop fasteners, for example. If the cleaning pads 18, 118 are not selectively removable from the cleaning heads 16, 116, respectively, the cleaning pads 18, 118 can be connected with the cleaning heads 16, 116 by any suitable mechanical connector, such as screws, hooks, straps, or clamps, for example or non-mechanical connector, such as an adhesive, for example. The cleaning pads 18, 118 do not have to be mounted to a cleaning head, rather it can also be mounted directly on the housing of the cleaning device 10, 110.

The cleaning heads 16, 116 can also be removably connected with the cleaning devices 10, 110, respectively. The removable cleaning heads 16, 116 can be interchangeable with other cleaning heads of different shapes and sizes suitable for a variety of cleaning environments and scenarios. The cleaning heads 16, 116 can be removably connected with the cleaning devices 10, 110, respectively, by any suitable mechanical connectors such as screws, hooks, straps, clamps or hook and loop tape, such as Velcro® hook and loop connectors, for example. If the cleaning heads 16, 116 are not selectively removable from the cleaning devices 10, 110, respectively, the cleaning heads 16, 116 can be connected with the cleaning devices by any suitable mechanical connector, such as screws, hooks, straps, or clamps, for example or chemical fasteners, such as an adhesive or weld, for example.

The stick-mounted and hand-held cleaning devices 10, 110 provide the user with the ability to generate bleach on demand and deliver the bleach to a cleaning pad 18, 118 for cleaning and disinfecting a surface. The generation of bleach on demand provides a cleaning device that is easy to use and does not require the user to store large amounts of bleach which can take up storage room and also be a safety hazard. In addition, on-demand generation of bleach negates the necessity of pouring or spraying bleach into a container or device for cleaning or directly onto the surface to be cleaned. This minimizes spills or inadvertent exposure of surfaces to bleach that can result in the bleaching of fabrics, such as clothing and carpet, for example.

While the invention has been specifically described in connection with certain specific embodiments thereof, it is to be understood that this is by way of illustration and not of limitation. Reasonable variation and combination are possible with the scope of the foregoing disclosure without departing from the spirit of the invention, which is defined in the appended claims.

What is claimed is:

1. A surface cleaning device comprising:
a source for an electrolyte solution;
a cleaning pad in fluid communication with the source for delivering a cleaning fluid to a surface to be cleaned;
an electrolytic cell comprising at least one anode and at least one cathode, with the at least one anode and the at least one cathode formed at least in part in the cleaning pad, for generating a bleach solution within the cleaning pad for application by the cleaning pad to the surface to be cleaned; and
a cleaning head, wherein the cleaning pad is mounted to the cleaning head and the at least one anode and at least one cathode are mounted to the cleaning head and extend at least partially into the cleaning pad for generating the bleach solution in situ in the cleaning pad.

2. The surface cleaning device according to claim 1 wherein the source comprises a refillable tank and further comprising a salt chamber for holding salt for making an electrolyte solution when water passes through the chamber, the salt chamber further having an inlet opening connected to the refillable tank and an outlet opening connected to the electrolytic cell.

3. The surface cleaning device according to claim 1 wherein the source includes a portion of the cleaning pad.

4. The surface cleaning device according to claim 1 wherein the source is a tank that is separate from the cleaning pad.

5. The surface cleaning device according to claim 1 wherein the cleaning pad is washable.

6. The surface cleaning device according to claim 1 wherein the cleaning pad is disposable.

7. The surface cleaning device according to claim 1 and further comprising a sensor for determining a characteristic of the electrolytic cell related to an amount of bleach in the electrolytic cell.

8. The surface cleaning device according to claim 7 wherein the characteristic of the electrolytic cell comprises one of a temperature, pH or potential of the electrolyte solution.

9. The surface cleaning device according to claim 7 wherein the sensor is connected to an indicator for informing a user of the amount of bleach in the electrolytic cell.

10. The surface cleaning device according to claim 9 wherein the indicator is adapted to inform a user when the amount of bleach in the electrolytic cell reaches a predetermined value.

11. The surface cleaning device according to claim 9 wherein the indicator is adapted to inform the user of a range of an amount of bleach in the electrolytic cell.

12. The surface cleaning device according to claim 9 and further comprising a controller connected to the sensor and the indicator and the controller has a program for comparing a signal from the sensor with stored acceptable values or ranges of values and generating a display signal representative of the amount of bleach in the electrolytic cell.

13. The surface cleaning device according to claim 1 and further comprising a foot assembly mounting the cleaning pad and a handle assembly pivotally mounted to the foot assembly and the source forms a part of the handle assembly.

14. The surface cleaning device according to claim 1 and further comprising a housing adapted to be held in a user's hand including a power supply housing and a cleaning head with the cleaning pad attached to the cleaning head.

15. The surface cleaning device according to claim 1 wherein at least one of the at least one anode and at least one cathode are connected to a power supply and are positioned at least partially within the cleaning pad, whereby the electrolytic cell is formed at least in part in the cleaning pad.

16. The surface cleaning device according to claim 15 wherein the cleaning pad comprises a sponge that is adapted to hold the electrolyte solution.

17. The surface cleaning device according to claim 16 and further comprising a tank for a cleaning solution and the tank is fluidly connected to the cleaning pad.

18. The surface cleaning device according to claim 15 wherein the power supply includes a rechargeable battery.

19. The surface cleaning device according to claim 15 wherein power supply is a disposable battery.

20. The surface cleaning device according to claim 15 wherein the power supply is derived from a power outlet.

21. The surface cleaning device according to claim 1 and further comprising an actuator connected to the electrolytic cell for selectively controlling the generation of bleach.

22. The surface cleaning device according to claim 21 and further comprising an electric pump to move the electrolyte solution between the source and the cleaning pad.

23. The surface cleaning device according to claim 21 and further comprising a squeeze pump to move the electrolyte solution between the source and the cleaning pad.

24. The surface cleaning device according to claim 21 and further comprising a gravity flow system to move the electrolyte solution between the source and the cleaning pad.

25. The surface cleaning device according to claim 1 wherein the electrolyte solution is a mixture of sodium chloride and water.

26. The surface cleaning device according to claim 25 wherein the electrolyte solution further comprises a detergent.

* * * * *